United States Patent
Malkowski

(10) Patent No.: US 11,779,713 B2
(45) Date of Patent: Oct. 10, 2023

(54) AIR PURIFIER FOR LAPAROSCOPIC SURGERY

(71) Applicant: Covidien LP, Mansfield, MA (US)

(72) Inventor: Jaroslaw T. Malkowski, Trumbull, CT (US)

(73) Assignee: COVIDIEN LP, Mansfield, MA (US)

( * ) Notice: Subject to any disclaimer, the term of this patent is extended or adjusted under 35 U.S.C. 154(b) by 1009 days.

(21) Appl. No.: 16/262,022

(22) Filed: Jan. 30, 2019

(65) Prior Publication Data

US 2019/0328983 A1    Oct. 31, 2019

Related U.S. Application Data

(60) Provisional application No. 62/662,248, filed on Apr. 25, 2018.

(51) Int. Cl.
*A61M 13/00*    (2006.01)

(52) U.S. Cl.
CPC ....... *A61M 13/006* (2014.02); *A61M 2205/07* (2013.01); *A61M 2205/7509* (2013.01);
(Continued)

(58) Field of Classification Search
CPC .. A61M 13/003; A61M 13/006; A61M 13/00; A61M 2205/07; A61M 2205/7509;
(Continued)

(56) References Cited

U.S. PATENT DOCUMENTS 5,643,200 A * 7/1997 Edwards ............. A61F 9/00736
                                                604/27
5,830,214 A * 11/1998 Flom ..................... A61M 1/774
                                                606/41
(Continued)

FOREIGN PATENT DOCUMENTS

| CN | 102091361 A | 6/2011 |
| CN | 107106737 A | 8/2017 |
| EP | 1188415 A2 | 3/2002 |

OTHER PUBLICATIONS

Chinese First Office Action dated Nov. 24, 2021 corresponding to counterpart Patent Application CN 2019103140389.
(Continued)

*Primary Examiner* — Emily L Schmidt
*Assistant Examiner* — Alexandra Lalonde
(74) *Attorney, Agent, or Firm* — CARTER, DELUCA & FARRELL LLP

(57) ABSTRACT

A surgical device includes a housing and an elongate body extending distally from the housing. The housing defines a filter chamber and a pump chamber therein, the filter chamber in fluid communication with the pump chamber. A filter assembly is disposed within the filter chamber, and a pump is disposed within the pump chamber. The elongate body defines first and second lumens therethrough, and includes at least one first opening in fluid communication with the first lumen and at least one second opening in fluid communication with the second lumen. The first lumen is in fluid communication with the filter chamber of the housing and the second lumen is in fluid communication with the pump chamber of the housing thereby forming a closed filtration loop through the surgical device.

20 Claims, 9 Drawing Sheets

(52) U.S. Cl.
CPC ............... *A61M 2205/7518* (2013.01); *A61M 2205/7536* (2013.01)

(58) Field of Classification Search
CPC .. A61M 2205/7518; A61M 2205/7536; A61M 25/003; A61M 1/0058; A61M 1/0023; A61M 2005/1657; A61M 5/165; A61M 1/76; A61M 1/77; A61M 1/774; A61M 1/78; A61M 1/784; A61M 1/28; A61M 1/281; A61M 1/282; A61M 1/284; A61M 1/285; A61M 1/287; A61M 1/288; A61M 1/159; A61M 39/06; A61M 2039/062; A61M 2039/0626; A61B 17/3474; A61B 2218/008; A61B 2218/007; A61B 2218/001; A61B 2017/3437; A61B 2017/3447; A61B 2017/3474; B01D 46/00; B01D 46/56; B01D 50/00
See application file for complete search history.

(56) References Cited

U.S. PATENT DOCUMENTS

| | | | |
|---|---|---|---|
| 6,685,665 B2* | 2/2004 | Booth | A61B 17/3421 604/158 |
| 2002/0128603 A1 | 9/2002 | Booth et al. | |
| 2005/0000196 A1 | 1/2005 | Schultz | |
| 2008/0167645 A1* | 7/2008 | Woloszko | A61B 18/1206 606/40 |
| 2012/0150101 A1 | 6/2012 | Stearns et al. | |
| 2014/0163489 A1* | 6/2014 | Walti | A61M 1/0058 604/319 |
| 2016/0106952 A1 | 4/2016 | Mastri et al. | |
| 2019/0008370 A1* | 1/2019 | Hino | A61B 1/00094 |

OTHER PUBLICATIONS

Extended European Search Report dated Aug. 13, 2019 corresponding to counterpart Patent Application EP 19170926.0.

* cited by examiner

AIR PURIFIER FOR LAPAROSCOPIC SURGERY

CROSS-REFERENCE TO RELATED APPLICATION

This application claims the benefit of and priority to U.S. Provisional Patent Application No. 62/662,248 filed Apr. 25, 2018, the entire disclosure of which is incorporated by reference herein.

BACKGROUND

1. Technical Field

The present disclosure relates generally to surgical devices. More particularly, the present disclosure relates to laparoscopic instruments including a closed loop air filtration system for circulating and filtering air within a body cavity.

2. Background of Related Art

Minimally invasive surgical procedures, including both endoscopic and laparoscopic procedures, permit surgery to be performed on organs, tissues, and vessels far removed from an opening within the tissue. Laparoscopic and endoscopic procedures generally require that any instrumentation inserted into the body be sealed, e.g., provisions may be made to ensure that gases do not enter or exit the body through the incision as, for example, in surgical procedures in which the surgical region is insufflated. Laparoscopic and endoscopic procedures generally utilize long and narrow instruments capable of reaching remote regions within the body and configured to seal with the incision or tube they are inserted through. Additionally, the instruments must be capable of being actuated remotely, that is, from outside the body.

In laparoscopic procedures, surgery is performed in the abdomen through a small incision in the body. The surgical environment may be contaminated with unhealthy fumes and/or impurities exhausted from the abdominal cavity during and/or after the laparoscopic procedure, and operating room staff may be exposed to these unhealthy fumes and impurities which may have adverse effects on the health of the operating room staff.

Thus, a need exists for a device that eliminates or reduces unhealthy exhaust of gases from the abdominal cavity.

SUMMARY

A surgical device in accordance with aspects of the present disclosure includes a housing and an elongate body extending distally from the housing. The housing defines a filter chamber and a pump chamber therein, the filter chamber in fluid communication with the pump chamber. A filter assembly is disposed within the filter chamber, and a pump is disposed within the pump chamber. The elongate body defines first and second lumens therethrough, and includes at least one first opening in fluid communication with the first lumen and at least one second opening in fluid communication with the second lumen. The first lumen is in fluid communication with the filter chamber of the housing and the second lumen is in fluid communication with the pump chamber of the housing thereby forming a closed filtration loop through the surgical device.

The at least one first opening or the at least one second opening of the elongate may include a tip opening defined in a distal end of the elongate body and/or a side opening defined through a sidewall of the elongate body.

In embodiments, the housing includes an outlet channel defined therein that fluidly couples the pump chamber of the housing with the second lumen of the elongate body.

The filter chamber may be positioned in a distal portion of the housing adjacent a proximal portion of the elongate body and the pump chamber may be positioned proximal of the filter chamber. The outlet channel may extend from the pump chamber distally past the filter chamber and be connected to the proximal portion of the elongate body.

In embodiments, the filter assembly includes a filter permeable to gas. The filter may be positioned within the filter chamber along a plane orthogonal to a longitudinal axis of the housing. In some embodiments, the filter assembly includes a plurality of filters. The plurality of filters may include at least one of a bacteria control filter, a virus control filter, or an odor control filter.

The housing may include a port operably coupled to the pump, the port configured to releasably engage an energy transmission line for actuating the pump. In some embodiments, the surgical device includes an energy transmission line operably coupled to the pump.

In embodiments, the pump is an air pump. The pump may be a mechanical air pump and the energy transmission line may be tubing configured for coupling with a vacuum. In some embodiments, the pump is a double diaphragm pump.

The pump may include a first suction port in fluid communication with the filter chamber and a second suction port in fluid communication with an insufflation fluid. The pump may include a control unit for selectively controlling the opening and closing of the first and second suction ports such that when the first suction port is open, the pump is configured to circulate air into the first lumen, through the filter chamber, and out the second lumen and, when the second suction port is open, the pump is configured to pressurize the insufflation fluid and discharge the insufflation fluid out through the second lumen.

The housing may further include a second pump chamber defined therein. The second pump chamber may include a second pump disposed therein. The second pump may include a suction port for drawing ambient air into the second pump and a discharge port in fluid communication with the second lumen of the elongate body.

A method of filtering air during a laparoscopic surgical procedure, in accordance with aspects of the present disclosure, includes: positioning an elongate body of a surgical device within a body cavity, the surgical device including: a housing defining a filter chamber and a pump chamber therein, the filter chamber in fluid communication with the pump chamber; a filter assembly disposed within the filter chamber; a pump disposed within the pump chamber; and the elongate body extending distally from the housing, the elongate body defining first and second lumens therethrough, the elongate body including at least one first opening in fluid communication with the first lumen and at least one second opening in fluid communication with the second lumen, the first lumen in fluid communication with the filter chamber of the housing and the second lumen in fluid communication with the pump chamber of the housing; and activating an energy source coupled to the pump of the surgical device to actuate the pump, wherein the pump draws air from the body cavity into the surgical device through the at least one first opening of the elongate body, cleans the air in the filter chamber, and returns the air back into the body cavity through the at least one second opening of the elongate body.

Embodiments of the present disclosure can include one or more of the following advantages.

The surgical device includes a closed air filtration loop for eliminating or reducing the exhaust of potentially hazardous substances from a body cavity, and the exposure thereof to operating room staff.

In embodiments, the filter chamber is disposed on a suction side of the pump chamber to prevent or reduce the introduction of contaminants and/or impurities into the pump and thus, in the air circulated back into the body cavity.

In some embodiments, the pump is configured to pressurize the cleaned air to further insufflate the body cavity in addition to the circulating and filtering the air of the body cavity.

Other aspects, features, and advantages will be apparent from the description, the drawings, and the claims.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
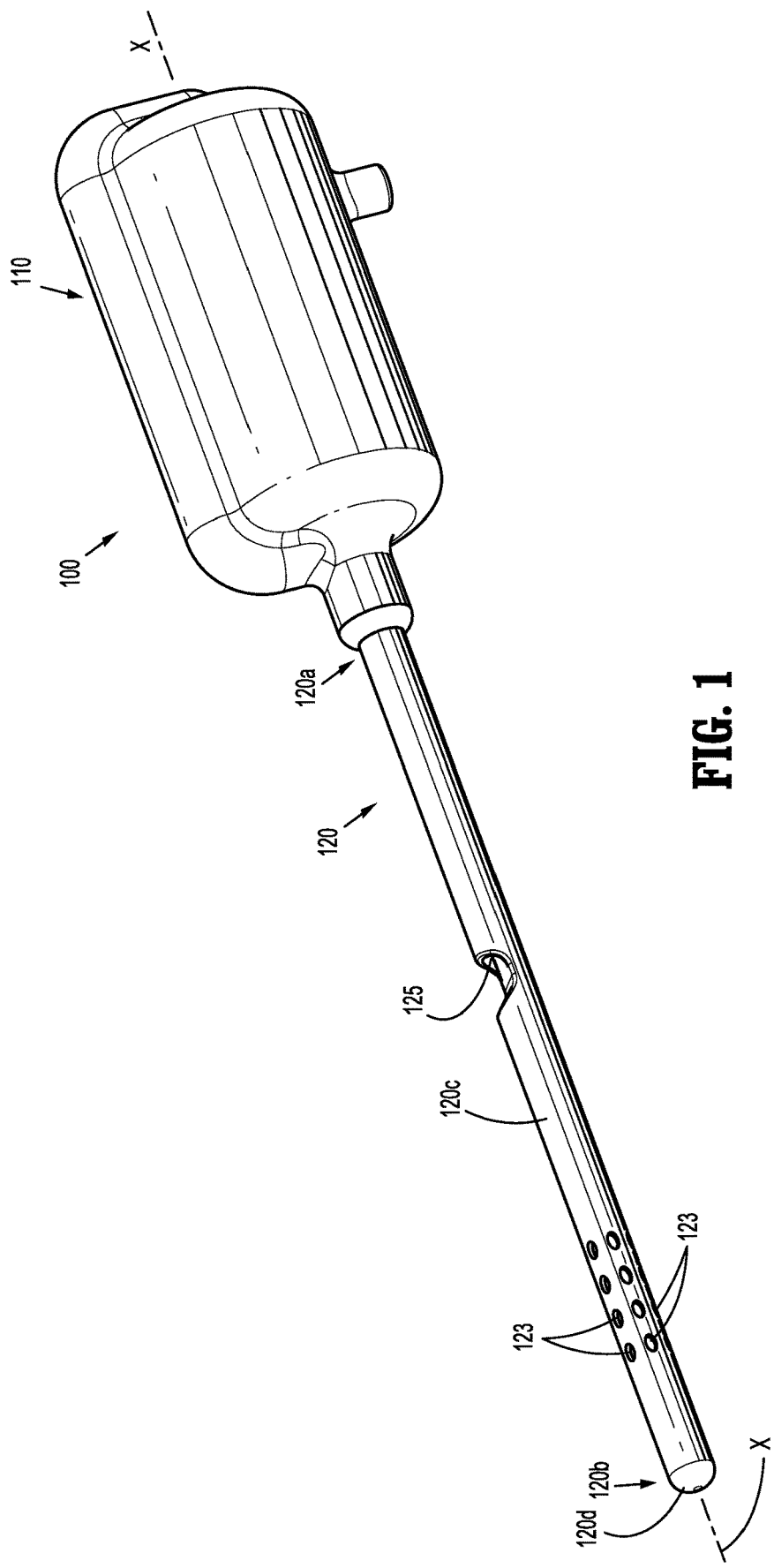
FIG. 1 is a perspective view of a surgical device in accordance with an embodiment of the present disclosure.

Embodiments of the present disclosure are now described in detail with reference to the drawings in which like reference numerals designate identical or corresponding elements in each of the several views. Throughout this description, the term "proximal" refers to a portion of a device, or component thereof, that is closer to a user, and the term "distal" refers to a portion of the device, or component thereof, that is farther from the user.

Referring now to FIG. 1, a surgical device 100, in accordance with an embodiment of the present disclosure, is in the form of a laparoscopic air filtration instrument. The surgical device 100 includes a handle or housing 110 and an elongate body or shaft 120 extending distally from the housing 110 along a longitudinal axis "X." The housing 110 is sized for engagement (e.g., holding/handling) by a user.

Figure 2:
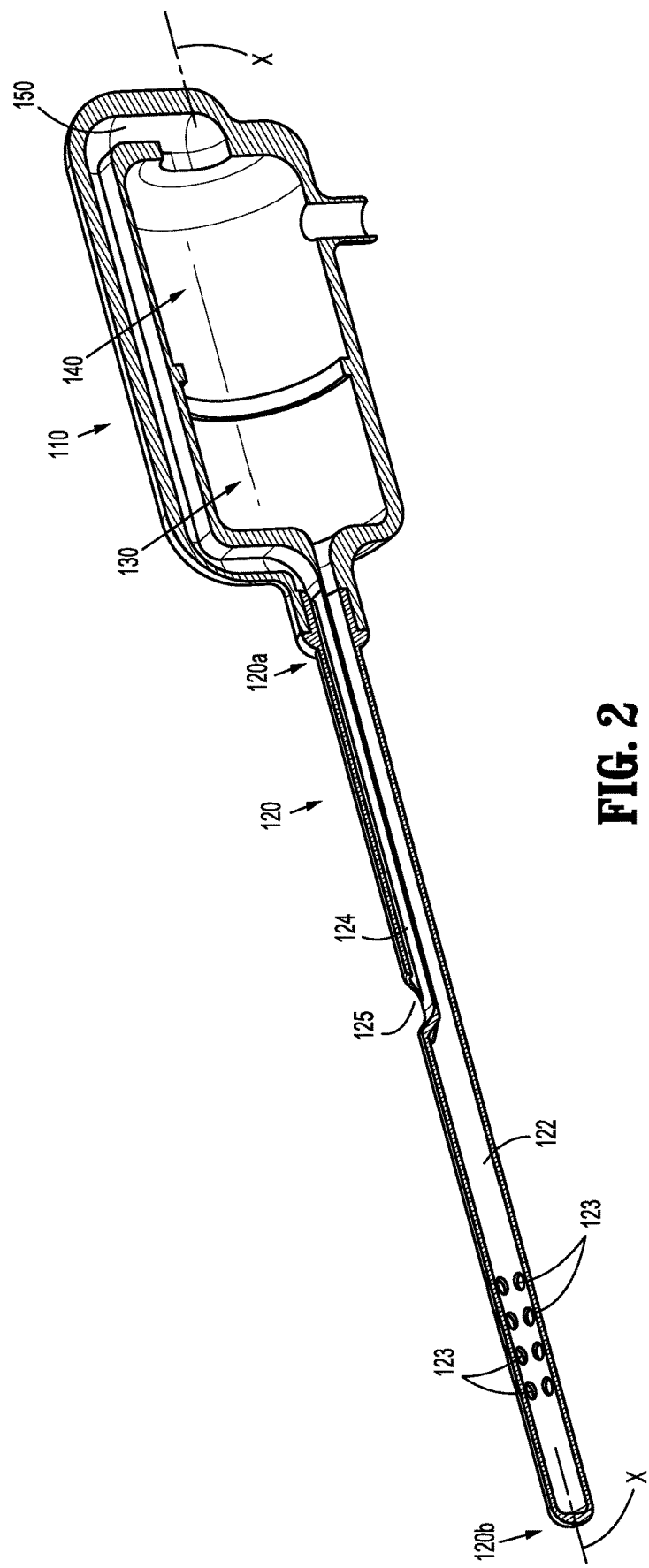
FIG. 2 is a cross-sectional view of the surgical device of FIG. 1, with components disposed within a handle housing of the surgical device removed.

As shown in FIGS. 1 and 2, the elongate body 120 defines a first or inlet lumen 122 and a second or outlet lumen 124 therethrough that are separate from each other and extend along (e.g., parallel to) the longitudinal axis "X" of the surgical device 100. The elongate body 120 includes a proximal portion 120a coupled to the housing 110 and a distal or tip portion 120b. One or more first or inlet openings 123 are defined in the elongate body 120 and are in fluid communication with the first lumen 122, and one or more second or outlet openings 125 are defined in the elongate body 120 and are in fluid communication with the second lumen 124. The first openings 123 are defined through a side wall 120c of the elongate body 120 in radially and longitudinally spaced relation relative to each other and to a closed distal end 120d of the elongate body 120, and the second opening 125 is defined through the sidewall 120c of the elongate body 120 in longitudinally spaced relation relative to the first openings 123.

Figure 3:
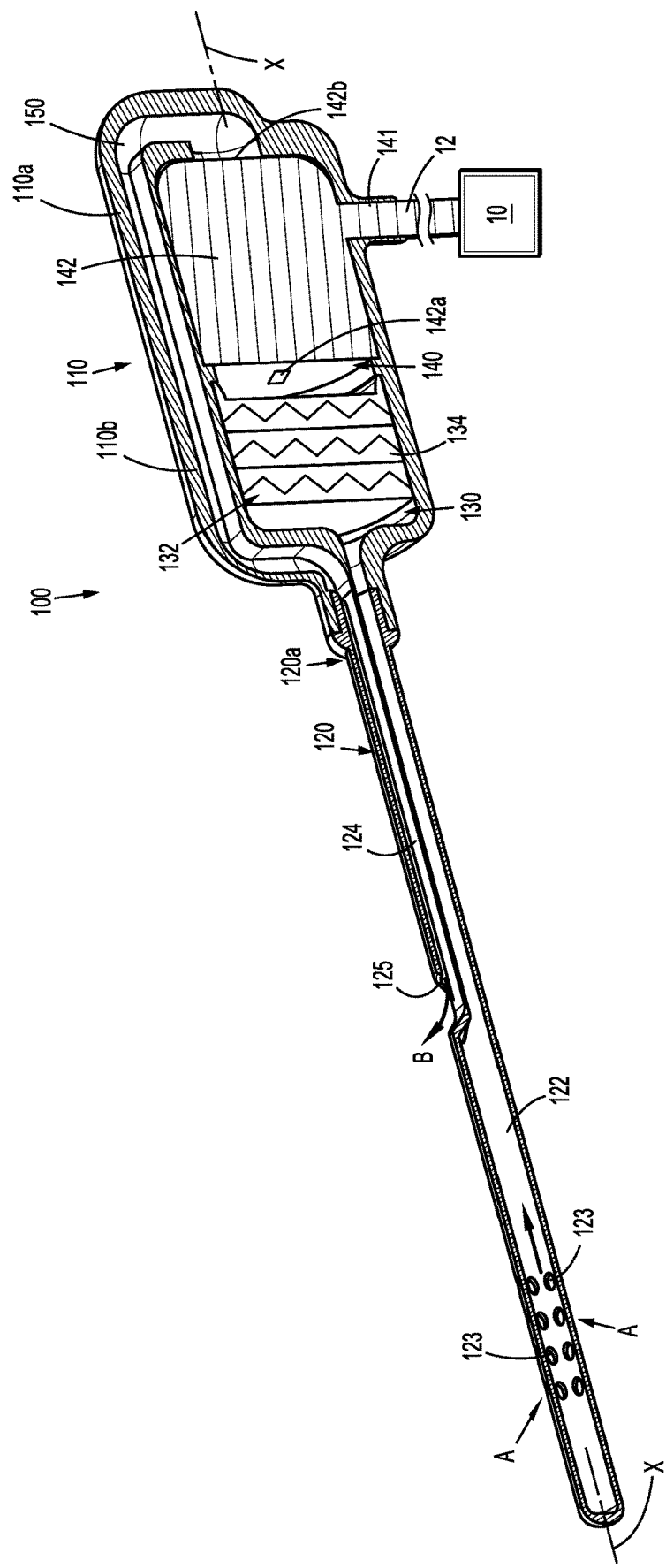
FIG. 3 is a cross-sectional view of the surgical device of FIG. 1.

As shown in FIGS. 2 and 3, the housing 110 of the surgical device 100 includes a filter chamber 130, a pump chamber 140, and an outlet channel 150 defined therein. The filter chamber 130 is in fluid communication with the pump chamber 140 which, in turn, is in fluid communication with the outlet channel 150. The first lumen 122 of the elongate body 120 is in fluid communication with the filter chamber 130 to provide directional flow, e.g., an inlet flow path, in the direction of arrows "A" into the first opening(s) 123 of the elongate body 120, through the first lumen 122 of the elongate body 120, and into the filter chamber 130 and then the pump chamber 140 of the housing 110. The second lumen 124 of the elongate body 120 is in fluid communication with the outlet channel 150 to provide directional flow, e.g., an outlet flow path, in the direction of arrows "B" from the pump chamber 140, through the outlet channel 150 of the housing 110, into the second lumen 124, and out of the second opening 125 of the elongate body 120.

The filter chamber 130 may be positioned in a distal portion 110b of the housing 110, adjacent the proximal portion 120a of the elongate body 120, and the pump chamber 140 may be positioned proximal of the filter chamber 130 in a proximal portion 110a of the housing 110. The outlet channel 150 may extend from the pump chamber 140 in the proximal portion 110a of the housing distally past the filter chamber 130 to the proximal portion 120a of the elongate body 120.

As shown in FIG. 3, the filter chamber 130 includes a filter assembly 132 disposed therein. The filter assembly 132 includes one or more filters 134 configured to remove contaminants and/or impurities from fluid (e.g., air) passing therethrough. The filter assembly 132 may include one or more filter cartridges removably insertable into the filter chamber 130 such that the filter assembly 132 can be a disposable and replaceable component of the surgical device 100.

The filters 134 of the filter assembly 132 are formed to be permeable to gas and impermeable to liquid. The filters 134 may be positioned within the filter chamber 130 along planes orthogonal to the longitudinal axis "X" of the surgical device 100, and in spaced relation relative to each other such that the air moving therethrough passes through each of the filters 134. The filters 134 may be textured (e.g., include baffles or pleats) to increase the filtering surface area of the filters 134.

The filters 134 of the filter assembly 132 may be the same or different for capturing and/or removing a variety of potentially hazardous substances (e.g., particulates, compounds, microorganisms, cellular matter, etc.) such as, for example, viruses, bacteria, and toxic vapors or fumes, by the same or different filtration and/or purification mechanisms. The filter assembly 132 may provide, for example, bacteria control, virus control, cancerogenic control, and/or odor control air purification. The filter assembly 132 may include therapeutic or pharmacological agent(s), such as antimicrobials, antibacterials, antiseptics, astringents, and/or disinfectants. The filter assembly 132 may include a combination of filtering profiles to target different contaminants. The filters 134 of filter assembly 132 may include carbon or carbon-based compounds for removing any of the potentially hazardous substances disclosed herein or known by those skilled in the art.

The pump chamber 140 includes a pump 142 disposed therein that is configured to move fluid (e.g., air) through the surgical device 100. The pump 142 includes a suction port 142a for passage of air from the filter chamber 130 into the pump 142, and a discharge port 142b for passage of the air from the pump 142 into the outlet channel 150.

The pump 142 is an air pump which may be in the form of a diaphragm pump, a bellows pump, an air turbine pump, among other mechanical or electrical devices within the purview of those skilled in the art for facilitating gas transfer. In embodiments in which the pump 142 is a mechanical air pump, the surgical device 100 can be a disposable (e.g., single-use) unit. In embodiments in which the pump 142 is an electric air pump, the housing 110 can be a reusable/sterilizable component of the surgical device 100 and other components, such as the elongate body 120 and/or the filter assembly 132, may be disposable and/or replaceable.

The pump 142 is driven by an external energy source 10 that is interconnected with the pump 142 by an energy transmission line 12. The energy transmission line 12 may releasably engage a port 141 defined in the housing 110 of the surgical device 100 for coupling with the pump 142 such that the energy transmission line 12 can be a disposable and/or replaceable component for use with the surgical device 100.

The pump 142 is a vacuum driven air pump adapted to maintain or draw adequate vacuum levels for circulating air through the surgical device 100. In embodiments in which the pump 142 is a mechanical air pump, the energy source 10 is a vacuum source and the energy transmission line 12 is tubing. In embodiments in which the pump 142 is an electric air pump, the energy source 10 is an electricity source and the energy transmission line 12 is a power cord.

Figure 4:
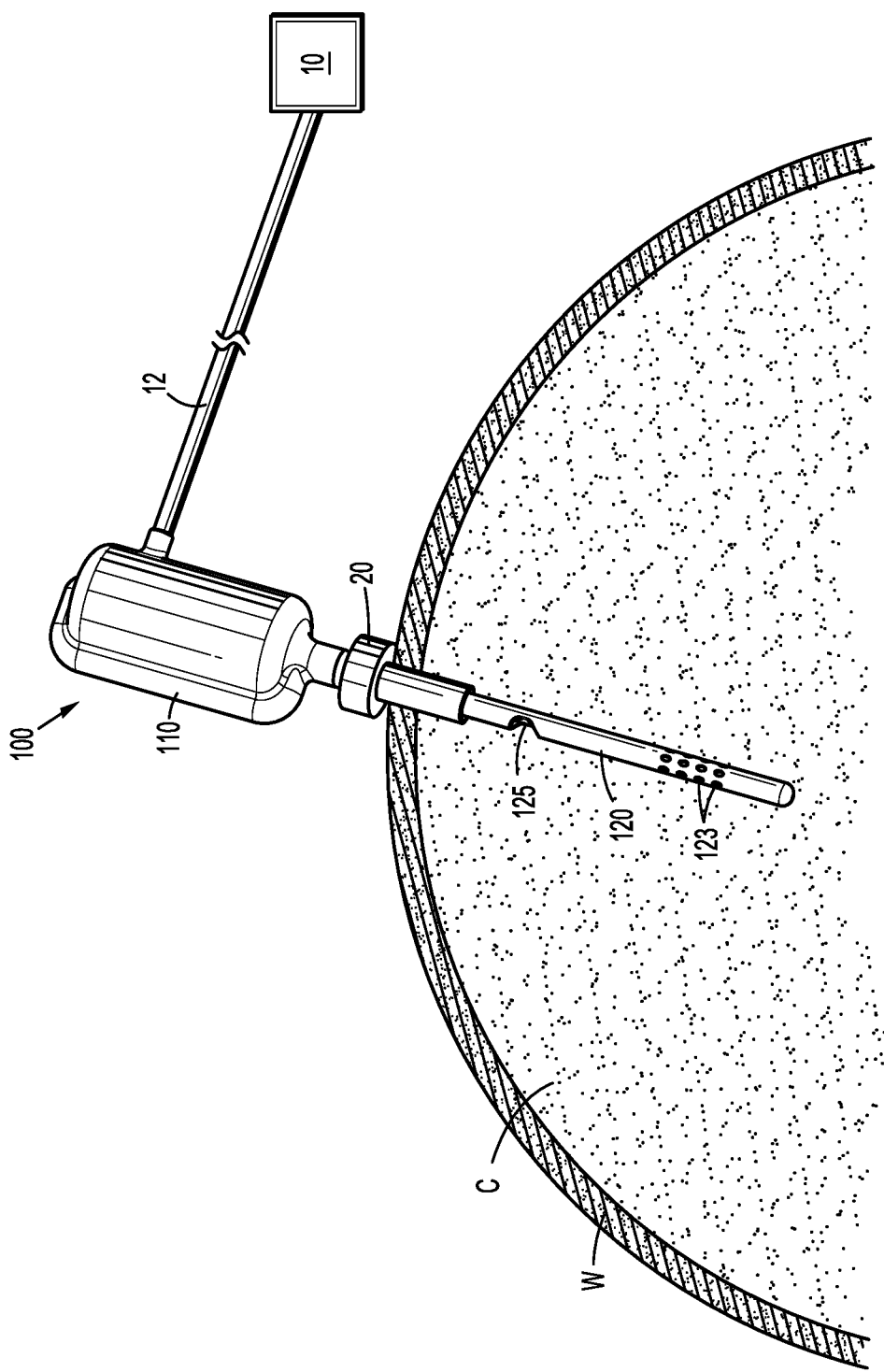
FIG. 4 is a perspective view of the surgical device of FIG. 1 positioned through an access device that is disposed within a body wall in accordance with an embodiment of a method of use of the present disclosure.

As shown in FIG. 4, in conjunction with FIG. 3, in a method of use in accordance with an embodiment of the present disclosure, the surgical device 100 is inserted through an access device 20 that is positioned through an abdominal wall "W" and into an abdominal cavity "C" of a patient. The access device 20 may be, for example, a trocar, a cannula, or an access port, such as a gel port or a SILS™ port of Covidien LP, configured to sealingly engage the surgical device 100 inserted therethrough, for example, to maintain insufflation of the abdominal cavity "C." The surgical device 100 is positioned within the access device 20 such that the first and second openings 123, 125 of the elongate body 120 are disposed within the abdominal cavity "C" and the housing 110 is positioned outside the abdominal wall "W."

The surgical device 100 is coupled to the energy source 10 via the energy transmission line 12, and the energy source 10 is activated to actuate the pump 142. The pump 142 draws air from the abdominal cavity "C" into the first lumen 122 of the elongate body 120 through the first openings 123, and into the filter chamber 130 of the housing 110. The air then passes through the filter assembly 132 disposed within the filter chamber 130, where the air is cleaned (e.g., filtered or purified), and the cleaned air passes into the pump chamber 140. The air then enters the pump 142 through the suction port 142a and is discharged from the pump 142 through the discharge port 142b into the outlet channel 150. The air travels through the outlet channel 150, into the second lumen 124, and out of the second opening 125 back into the abdominal cavity "C." Thus, a closed loop air filtration system is created in which the air of the abdominal cavity "C" is circulated (e.g., recirculated) and cleaned.

The configuration of the first openings 123 in the elongate body 120 minimizes or prevents bodily fluids and/or surrounding organs from being sucked into the first lumen 122 and/or damaged while the air is drawn from the abdominal cavity "C" into the elongate body 120. The configuration of the second opening 125 in longitudinally spaced relation relative to the first openings 123 reduces recirculation of air flow between the first and second openings 123, 125 (e.g., between the inlet and outlet flows) and increases the efficiency of the surgical device 100.

Figure 5:
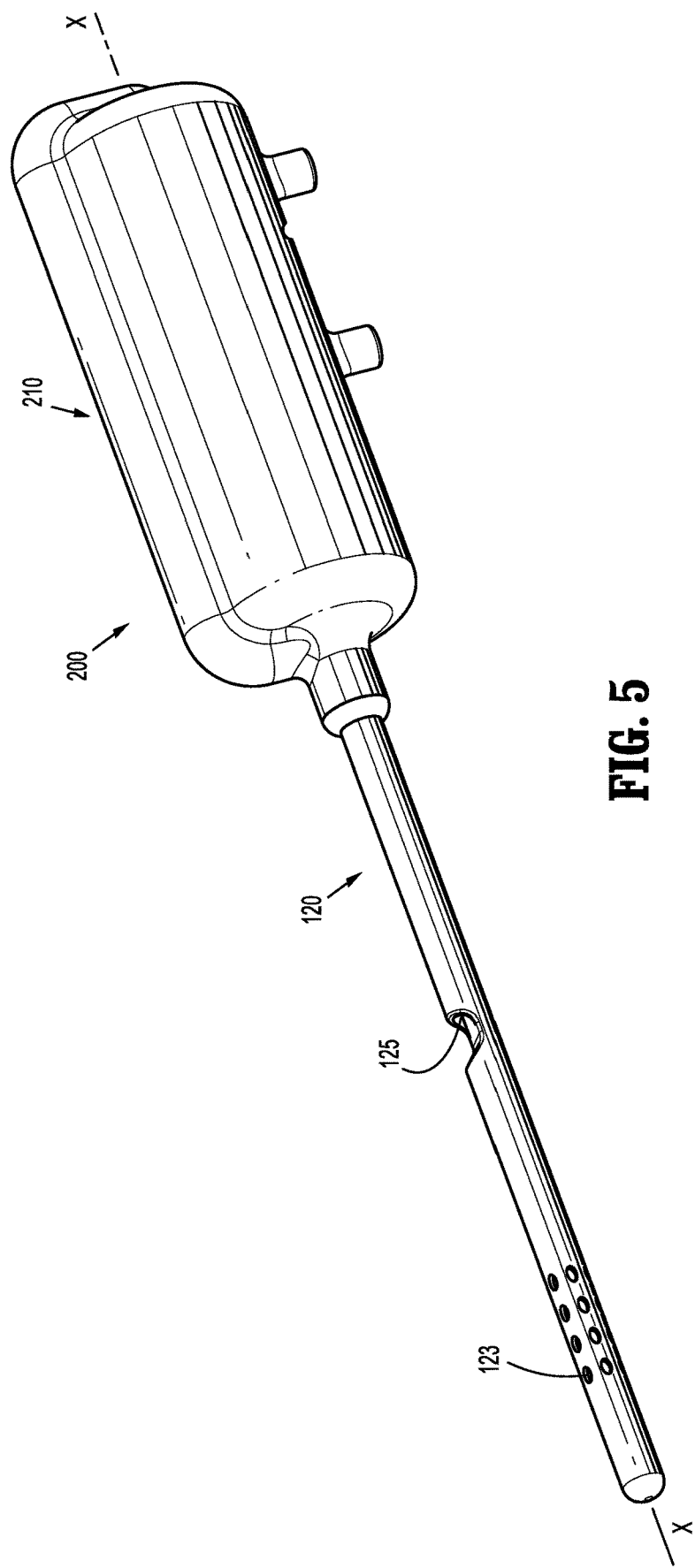
FIG. 5 is a perspective view of a surgical device in accordance with another embodiment of the present disclosure.

Turning now to FIG. 5, a surgical device 200, in accordance with another embodiment of the present disclosure, is in the form of a laparoscopic air filtration and insufflation instrument. The surgical device 200 is substantially similar to the surgical device 100 of FIG. 1 and will be described with respect to the differences therebetween.

Figure 6:
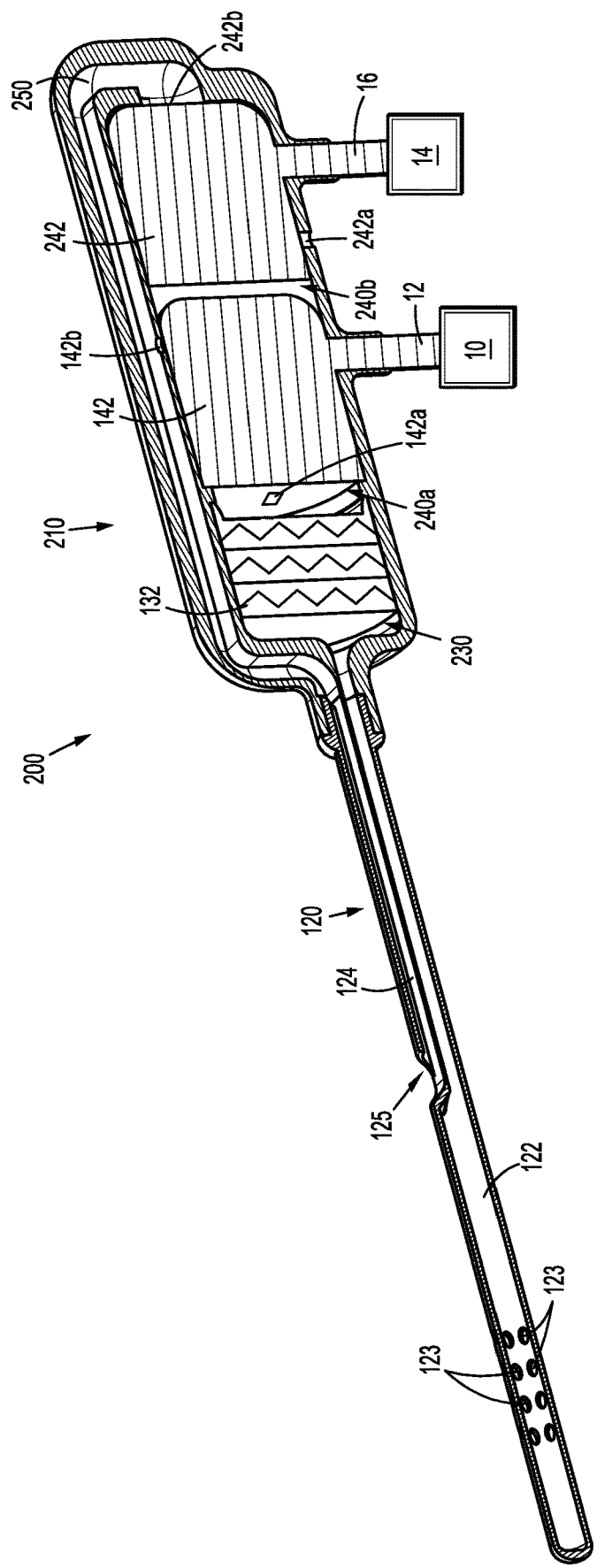
FIG. 6 is a cross-sectional view of the surgical device of FIG. 5.

As shown in FIGS. 5 and 6, the surgical device 200 includes a handle or housing 210 and an elongate body or shaft 120 extending distally from the housing 210 along a longitudinal axis "X." The housing 210 of the surgical device 200 includes a filter chamber 230, a first pump chamber 240a, a second pump chamber 240b, and an outlet channel 250 defined therein. The filter chamber 230 is in fluid communication with the first pump chamber 240a which, in turn, is in fluid communication with the outlet channel 250. The second pump chamber 240b is also in fluid communication with the outlet channel 250. The first lumen 122 of the elongate body 120 is in fluid communication with the filter chamber 230 to provide directional flow, e.g., an inlet flow path, into the first openings 123 and the first lumen 122 of the elongate body 120, and through the filter chamber 230 and the first pump chamber 240a of the housing 210. The second lumen 124 is in fluid communication with the outlet channel 250 to provide directional flow, e.g., an outlet flow path, from the first and/or second pump chambers 240a, 240b and the outlet channel 250 of the housing 210, into the second lumen 124 of the elongate body 120, and then out of the second opening 125 of the elongate body 120.

The filter chamber 230 includes a filter assembly 132 disposed therein, and the first pump chamber 240a includes a first pump 142 disposed therein that includes a suction port 142a for passage of air from the filter chamber 230 into the pump 142, and a discharge port 142b for passage of the air from the pump 142 into the outlet channel 250. The first pump 142 is driven by a first external energy source 10 and connected thereto by a first energy transmission line 12 to circulate and filter air of an abdominal cavity, as discussed above with regard to the surgical device 100.

The second pump chamber 240b includes a second pump 242 disposed therein that is configured to pressurize fluid (e.g., air) and move the pressurized fluid out of the surgical device 200 to insufflate an abdominal cavity. The second pump 242 includes a suction port 242a for the passage of an insufflation fluid (e.g., ambient air) into the second pump 242 and a discharge port 242b for passage of the insufflation fluid from the second pump 242 into the outlet channel 250. The second pump 242 may be a mechanical or electrical air pump, as described above with respect to pump 142, and is driven by a second external energy source 14 that is interconnected with the second pump 242 via a second energy transmission line 16. The second pump 242 may be the same as or different from the first pump 142 and/or may be coupled to the same energy source as the first pump 142 (e.g., the first external energy source 10). Accordingly, the first pump 142 is utilized to circulate purified air of an abdominal cavity and the second pump 242 is utilized to insufflate the abdominal cavity.

Figure 7:
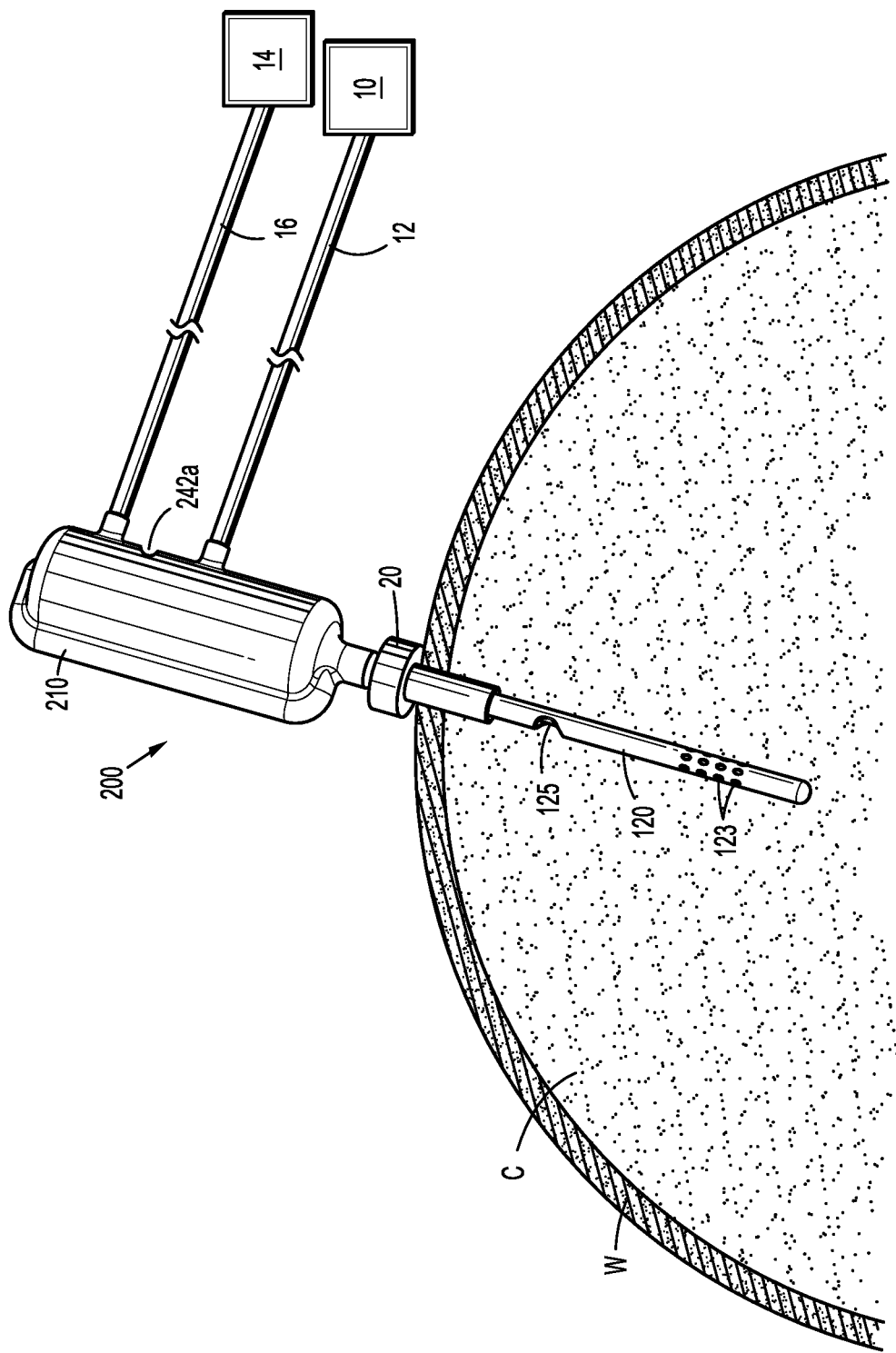
FIG. 7 is a perspective view of the surgical device of FIG. 5 positioned through an access device that is disposed within a body wall in accordance with an embodiment of a method of use of the present disclosure.

As shown in FIG. 7, in a method of use in accordance with an embodiment of the present disclosure, the surgical device 200 is inserted into an access device 20 that is positioned through an abdominal wall "W" and into an abdominal cavity "C" of a patient. The surgical device 200 is positioned within the access device 20 such that the first and second openings 123, 125 of the elongate body 120 are disposed within the abdominal cavity "C" and the housing 210 is positioned outside the abdominal wall "W."

With continued reference to FIG. 7, in conjunction with FIG. 6, the surgical device 200 is coupled to the first and second energy sources 10, 14 via the first and second energy transmission lines 12, 16, and the first and second energy sources 10, 14 are activated to actuate the first and second pumps 142, 242 disposed within the housing 210. The first pump 142 draws air from the abdominal cavity "C" into the first lumen 122 of the elongate body 120 through the first openings 123, and into the filter chamber 230 of the housing 210. The air then passes through the filter assembly 132 disposed within the filter chamber 230, where the air is cleaned (e.g., filtered or purified), and the cleaned air passes into the first pump 142 disposed in the first pump chamber 240a. The first pump 142 discharges the cleaned air through the discharge port 142b into the outlet channel 250, through the second lumen 124 of the elongate body 120, and out of the second opening 125 back into the abdominal cavity "C."

The second pump 242 draws ambient air into the second pump 242 through the suction port 242a where the air is pressurized. The pressurized air is discharged from the second pump chamber 240b through the discharge port 242b into the outlet channel 250, through the second lumen 124 of the elongate body 120, and out of the second opening 125 into the abdominal cavity "C." The second pump 242 is configured to maintain a pre-set pressure level within the abdominal cavity "C." In embodiments, the pre-set pressure level is up to about 25 mmHg, and in some embodiments, up to about 20 mmHg. In certain embodiments, the pre-set pressure level ranges from about 8 mmHg to about 14 mmHg. The pump 242 is configured to discharge pressurized air therefrom such that outlet flow path through the surgical device 200 is an insufflation flow path for creating and/or maintaining a pneumoperitoneum of the abdominal cavity, as well as circulating and cleaning air of the abdominal cavity in a closed circulation loop.

Figure 8:
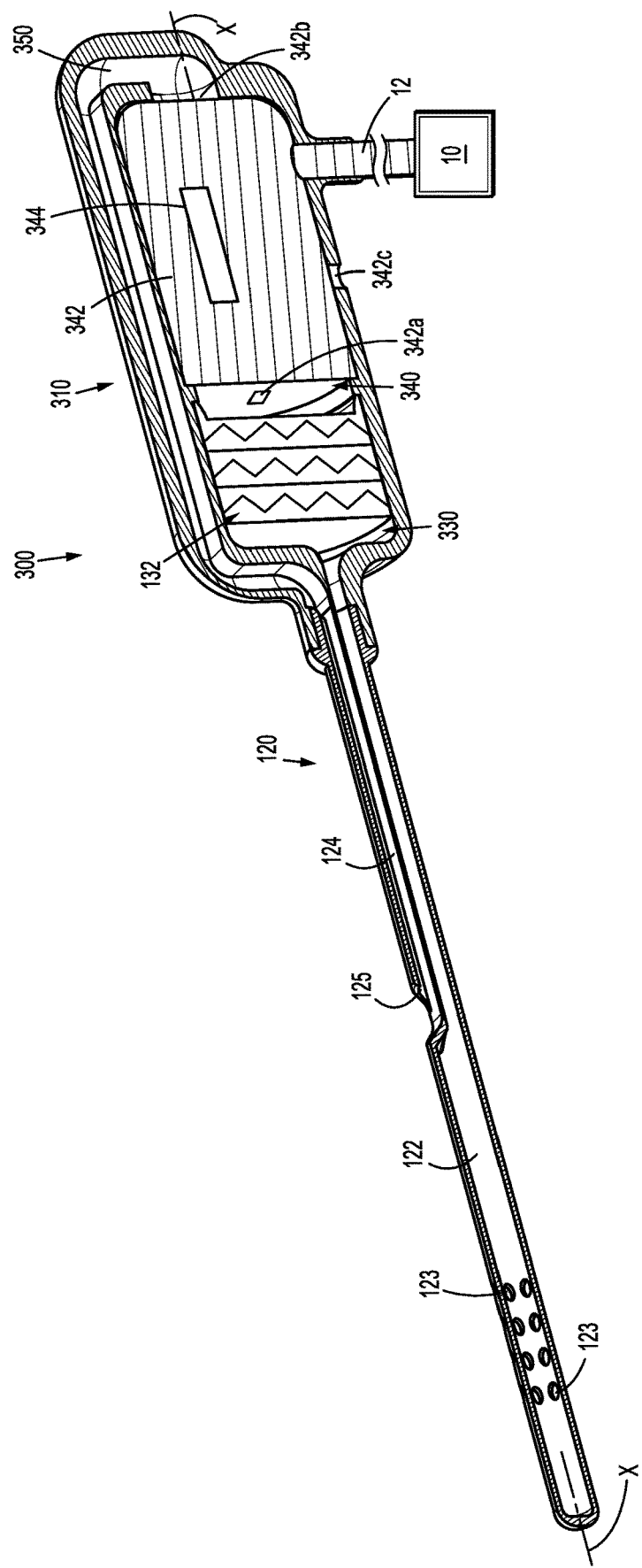
FIG. 8 is a cross-sectional view of a surgical device in accordance with yet another embodiment of the present disclosure.

With reference now to FIG. 8, a surgical device 300, in accordance with another embodiment of the present disclosure, is in the form of a laparoscopic air filtration and insufflation instrument. The surgical device 300 is substantially similar to the surgical device 200 of FIG. 5 and will be described with respect to the differences therebetween.

The surgical device 300 includes a handle or housing 310 and an elongate body or shaft 120 extending distally from the housing 310 along a longitudinal axis "X." The housing 310 of the surgical device 300 includes a filter chamber 330, a pump chamber 340, and an outlet channel 350 defined therein. The filter chamber 330 is in fluid communication with the pump chamber 340 which, in turn, is in fluid communication with the outlet channel 250. The first lumen 122 of the elongate body 120 is in fluid communication with the filter chamber 330 to provide directional flow, e.g., an inlet flow path, into the surgical device 300 through the first openings 123, and the second lumen 124 of the elongate body 120 is in fluid communication with the outlet channel 350 to provide direction flow, e.g., an outlet flow path, out of the surgical device 300 through the second opening 125.

The filter chamber 330 includes a filter assembly 132 disposed therein, and the pump chamber 340 includes a pump 342 disposed therein that is configured to purify and circulate and/or pressurize air. The pump 342 is an air pump, as discussed above with regard to pump 142, that is driven by an external energy source 10 and connected thereto by an energy transmission line 12 extending between the pump 342 and the energy source 10.

In the illustrated embodiment, the pump 342 is a double diaphragm pump including a first suction port 342a for passage of air from the filter chamber 330 into the pump chamber 340 and a discharge port 342b for passage of the air from the pump chamber 340 into the outlet channel 350. The pump 342 also includes a second suction port 342c for the passage of ambient air into the pump 342. The pump 342 includes a control unit 344 for alternating the function of the pump 342 between circulating and purifying air and pressurizing air. The control unit 344 is configured to switch from circulating and purifying air to pressurizing air in response to a drop in pressure from a pre-set pressure level or range. If the pressure drops below the pre-set pressure level or range, the control unit 344 will close the first suction port 342a and open the second suction port 342c such that the ambient air is drawn into the pump 342. If the pressure is at the pre-set pressure level or within range, the control unit 344 opens the first suction port 342a and closes the second suction port 342c to circulate and purify the air drawn into and withdrawn through the elongate body 120.

Accordingly, in a method of use, the surgical device 300 is inserted into an access device 20 (see e.g., FIG. 7), as discussed above with regard to surgical devices 100, 200. The surgical device 300 is coupled to the energy source 10 via the energy transmission line 12, and the energy source 10 is activated to actuate the pump 342 disposed within the housing 210. The pump 342 will then either circulate and purify the air disposed within the abdominal cavity "C" or insufflate the abdominal cavity "C" with pressurized air, as discussed above, in response to pressure changes within the abdominal cavity "C."

While the surgical devices 200, 300 have been described as discharging pressurized air into an abdominal cavity "C" through the outlet channel 250, 350 of the housing 210, 310 and the second lumen 124 of the elongate body 120, it should be understood that the surgical devices 200, 300 may be interconnected with a gas source as a source of insufflation fluid and/or the housing may include an insufflation channel in fluid communication with a third lumen of the elongate body. Such a configuration may allow for simultaneous or selective use of the filtering and insufflation functions of the surgical device.

Further, while the surgical devices have been described as being interconnected to an energy source via an energy transmission line, other power configurations are contemplated. For example, the energy source may be wirelessly coupled to the pump. As another example, the housing of the surgical device may include an energy source chamber defined therein in which the energy source (e.g., batteries) is disposed.

Other configurations of the elongate body of the surgical devices are envisioned. For example, while the elongate body has been shown as being substantially circular in cross-section (e.g., tubular), it should be appreciated that other cross-sectional areas of the elongate body, such as oval, elliptical, or polygonal shapes, are also with the scope of this disclosure. Additionally, the cross-sectional area and/or shape of the first and second lumens of the elongate body may be the same or different, and/or may vary along the length of the elongate body.

Figure 9:
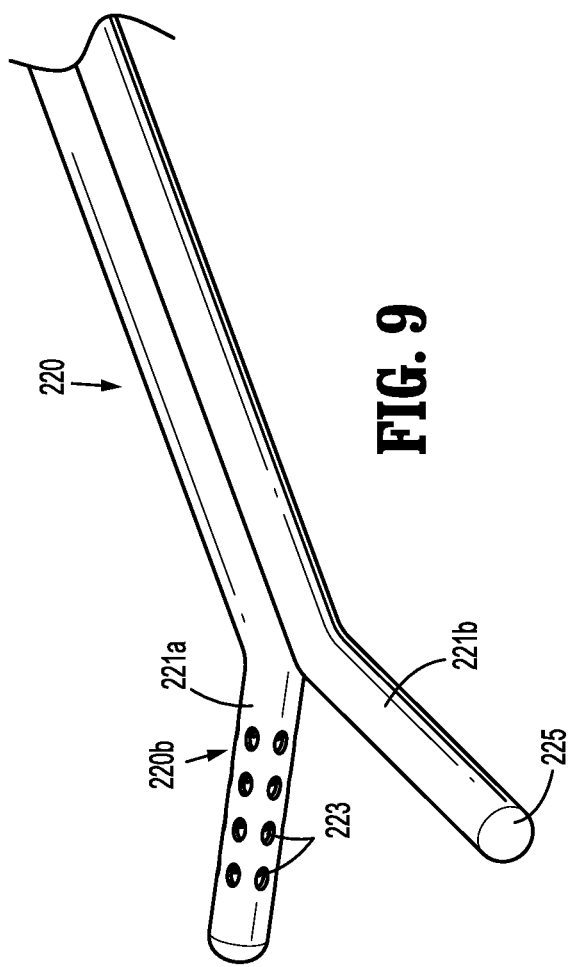
FIG. 9 is a perspective view of an elongate body of a surgical device in accordance with an embodiment of the present disclosure.

Further, while the first and second lumens of the elongate body are shown as being longitudinally staggered with respect to each other, it is contemplated that the first and second lumens may be coterminous with each other and/or may be split along a distal portion thereof, as shown for example, in FIG. 9. As shown in FIG. 9, a distal portion 220b of an elongate body 220 is split such that a first segment 221a includes first or inlet openings 223 and a second segment 221b includes a second or outlet opening 225. The first and second segments 221a, 221b would be movable from the biased split configuration to an aligned configuration to facilitate insertion into a body cavity (e.g., through an access device).

Figure 10:
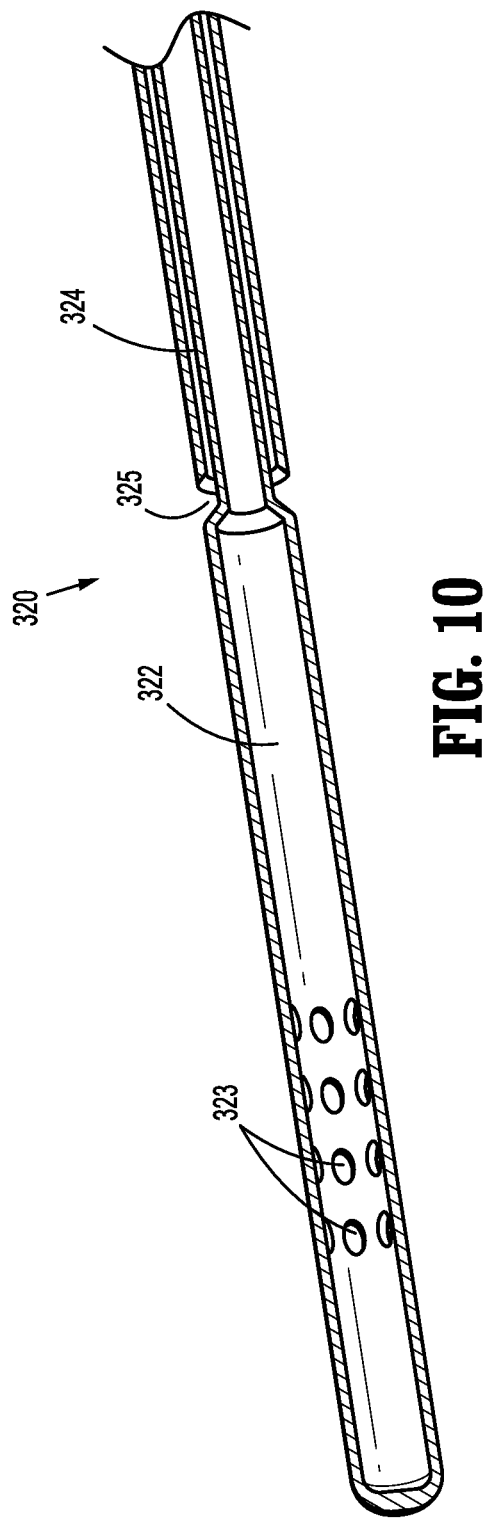
FIG. 10 is a cross-sectional view of an elongate body of a surgical device in accordance with another embodiment of the present disclosure.

In yet another example, as shown in FIG. 10, an elongate body 320 includes first and second lumens 332, 324 that are coaxially aligned and longitudinally staggered with respect to each other such that first or inlet openings 323 of the first lumen 332 are disposed distal to a second or outlet opening 325 of the second lumen 324. A staggered and/or split tip configuration may reduce air recirculation between the first and second openings of the elongate body.

Further, while the elongate bodies of the surgical devices have been shown as including first openings that are side openings and a second opening that is a side opening or a tip opening, it should be understood that various configurations of tip openings and/or side openings are contemplated. For example, the first lumen may additionally or alternatively include a tip opening and the second lumen may include a plurality of side and/or tip openings.

While the surgical device have been described as filtering air disposed within an abdominal cavity during a laparoscopic surgical procedure and/or maintaining insufflation of an abdominal cavity, other applications of such surgical devices are additionally or alternatively possible. For example, it should be appreciated that surgical devices of the present disclosure may be used in a range of minimally invasive surgical applications including, for example, removal of gaseous by-products associated with some surgical procedures (e.g., smoke evacuation associated with ablation and cautery procedures). As another example, the filter assembly of the surgical devices of the present disclosure may include a combination of filtering profiles expanding their use such as, for example, during laparoscopy training in cadaver labs to mainly eliminate or reduce odor but also target other dangers or impurities associated with the cadaver labs.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described. Thus, other embodiments are within the scope of the following claims.

What is claimed is:

1. A surgical device extending along a longitudinal axis between a proximal end of the surgical device and a distal-most end of the surgical device, the surgical device comprising:
   a housing defining a filter chamber and a pump chamber in the housing, the filter chamber in fluid communication with the pump chamber, wherein the housing forms a handle configured for holding and handling of the surgical device;
   a filter assembly disposed within the filter chamber;
   a pump disposed within the pump chamber; and
   an elongate body in the form of a shaft attached to and extending distally from the housing, the elongate body having a proximal end and a distal end, the distal end defining the distal-most end of the surgical device and configured for positioning within a body cavity, the elongate body defining first and second lumens through the elongate body, the elongate body including at least one first opening in fluid communication with the first lumen and at least one second opening in fluid communication with the second lumen, the first lumen in fluid communication with the filter chamber of the housing and the second lumen in fluid communication with the pump chamber of the housing thereby forming a closed filtration loop through the surgical device, the filter chamber, the pump chamber, and the elongate body axially aligned along the longitudinal axis of the surgical device.

2. The surgical device according to claim 1, wherein the at least one first opening or the at least one second opening of the elongate body includes a tip opening defined in the distal end of the elongate body.

3. The surgical device according to claim 1, wherein the at least one first opening or the at least one second opening of the elongate body includes a side opening defined through a sidewall of the elongate body, the sidewall extending between the proximal end and the distal end of the elongate body.

4. The surgical device according to claim 1, wherein an outlet channel is defined in the housing and extends from the pump chamber to the elongate body, the outlet channel fluidly coupling the pump chamber of the housing with the second lumen of the elongate body.

5. The surgical device according to claim 4, wherein the filter chamber is positioned in a distal portion of the housing adjacent a proximal portion of the elongate body and the pump chamber is positioned proximal of the filter chamber.

6. The surgical device according to claim 5, wherein the outlet channel extends from the pump chamber distally past the filter chamber and is connected to the proximal portion of the elongate body.

7. The surgical device according to claim 1, wherein the filter assembly includes a filter permeable to gas.

8. The surgical device according to claim 7, wherein the filter is positioned within the filter chamber along a plane orthogonal to the longitudinal axis of the surgical device.

9. The surgical device according to claim 1, wherein the filter assembly includes a plurality of filters.

10. The surgical device according to claim 9, wherein the plurality of filters includes at least one of a bacteria control filter, a virus control filter, or an odor control filter.

11. The surgical device according to claim 1, wherein the housing includes a port defined through the housing and opening into the pump chamber, the port configured to releasably engage an energy transmission line for actuating the pump.

12. The surgical device according to claim 1, further comprising an energy transmission line operably coupled to the pump.

13. The surgical device according to claim 12, wherein the pump is a mechanical air pump and the energy transmission line is tubing configured for coupling with a vacuum.

14. The surgical device according to claim 1, wherein the pump is an air pump.

15. The surgical device according to claim 1, wherein the pump is a double diaphragm pump.

16. The surgical device according to claim 1, wherein the pump includes a first suction port in fluid communication with the filter chamber and a second suction port in fluid communication with an insufflation fluid, the pump including a control unit for selectively controlling opening and closing of the first and second suction ports such that when the first suction port is open, the pump is configured to circulate air into the first lumen, through the filter chamber, and out the second lumen and, when the second suction port is open, the pump is configured to pressurize the insufflation fluid and discharge the insufflation fluid out through the second lumen.

17. The surgical device according to claim 1, wherein a second pump chamber is defined in the housing and a second pump is disposed in the second pump chamber, the second pump including a suction port for drawing ambient air into the second pump and a discharge port in fluid communication with the second lumen of the elongate body.

18. The surgical device according to claim 1, wherein the filter chamber and the pump chamber are directly connected with one another within the housing.

19. The surgical device according to claim 1, wherein the at least one first opening of the elongate body includes a plurality of first openings defined through a side wall of the elongate body in radially and longitudinally spaced relation relative to each other.

20. A method of filtering air during a laparoscopic surgical procedure, comprising:
 positioning an elongate body of a surgical device within a body cavity, the surgical device extending along a longitudinal axis between a proximal end of the surgical device and a distal-most end of the surgical device, the surgical device including:
  a housing defining a filter chamber and a pump chamber in the housing, the filter chamber in fluid communication with the pump chamber, wherein the housing forms a handle configured for holding and handling of the surgical device;
  a filter assembly disposed within the filter chamber;
  a pump disposed within the pump chamber; and
  the elongate body in the form of a shaft attached to and extending distally from the housing, the elongate body having a proximal end and a distal end, the distal end defining the distal-most end of the surgical device and configured for positioning within the body cavity, the elongate body defining first and second lumens through the elongate body, the elongate body including at least one first opening in fluid communication with the first lumen and at least one second opening in fluid communication with the second lumen, the first lumen in fluid communication with the filter chamber of the housing and the second lumen in fluid communication with the pump chamber of the housing thereby forming a closed filtration loop through the surgical device,
  the filter chamber, the pump chamber, and the elongate body axially aligned along the longitudinal axis of the surgical device; and
 activating an energy source coupled to the pump of the surgical device to actuate the pump, wherein the pump draws air from the body cavity into the surgical device through the at least one first opening of the elongate body, cleans the air in the filter chamber, and returns the air back into the body cavity through the at least one second opening of the elongate body.

* * * * *